United States Patent
Hansen et al.

(10) Patent No.: US 12,262,881 B2
(45) Date of Patent: Apr. 1, 2025

(54) MEDICAL DEVICE ROTATION ASSEMBLIES AND METHODS OF USING THE SAME

(71) Applicant: Boston Scientific Scimed, Inc., Maple Grove, MN (US)

(72) Inventors: Katrina Hansen, Denver, CO (US); Robb M. Gavalis, Westborough, MA (US); David Callaghan, Ashland, MA (US); Bernadette Durr, Santa Clara, CA (US); John B. Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/460,852

(22) Filed: Sep. 5, 2023

(65) Prior Publication Data

US 2023/0404556 A1 Dec. 21, 2023

Related U.S. Application Data

(63) Continuation of application No. 17/166,875, filed on Feb. 3, 2021, now Pat. No. 11,793,501.

(60) Provisional application No. 62/969,881, filed on Feb. 4, 2020.

(51) Int. Cl.
*A61B 17/00* (2006.01)
*A61B 17/34* (2006.01)

(52) U.S. Cl.
CPC ......... *A61B 17/00234* (2013.01); *A61B 2017/00318* (2013.01); *A61B 2017/00367* (2013.01); *A61B 17/3478* (2013.01)

(58) Field of Classification Search
CPC .... A61B 2017/2929; A61B 2017/2927; A61B 2017/2926; A61B 2017/0046; A61B 2017/2837; A61B 2017/293; A61B 2017/2909; A61B 2017/291; A61B 2017/2912; A61B 2017/2923; A61B 2017/2913; A61B 2017/2925; A61B 2017/2901; A61B 2017/2903; A61F 5/08
See application file for complete search history.

(56) References Cited

U.S. PATENT DOCUMENTS

| | | | |
|---|---|---|---|
| 4,874,371 | A | 10/1989 | Comben et al. |
| 5,462,527 | A | 10/1995 | Stevens-Wright et al. |
| 5,499,998 | A | 3/1996 | Meade |

(Continued)

FOREIGN PATENT DOCUMENTS

CN 109475289 A 3/2019

OTHER PUBLICATIONS

International Search Report and Written Opinion issued in International Application No. PCT/US2021/016391, issued May 19, 2021 (11 pages).

*Primary Examiner* — Majid Jamialahmadi
(74) *Attorney, Agent, or Firm* — Bookoff McAndrews, PLLC

(57) ABSTRACT

A medical device that includes a sheath, a tool within the sheath and movable relative to the sheath, and a handle including a rotation assembly configured to rotate the tool relative to the sheath in response to rotation of the rotation assembly relative to a portion of the handle. The rotation assembly rotates the tool relative to the sheath at predefined angular intervals and inhibits movement at each of the predefined angular intervals.

18 Claims, 8 Drawing Sheets

(56) References Cited

U.S. PATENT DOCUMENTS

| | | | |
|---|---|---|---|
| 5,954,736 A * | 9/1999 | Bishop | A61B 17/320092 |
| | | | 606/157 |
| 9,132,258 B2 | 9/2015 | Bednarek et al. | |
| 10,123,848 B2 | 11/2018 | Lawrence et al. | |
| 2008/0103412 A1 | 5/2008 | Chin | |
| 2019/0069759 A1 | 3/2019 | Govari et al. | |
| 2019/0083121 A1 | 3/2019 | Benamou et al. | |

\* cited by examiner

MEDICAL DEVICE ROTATION ASSEMBLIES AND METHODS OF USING THE SAME

CROSS-REFERENCE TO RELATED APPLICATIONS

This application is a continuation of U.S. application Ser. No. 17/166,875, filed on Feb. 3, 2021, which claims the benefit of priority from U.S. Provisional Application No. 62/969,881, filed Feb. 4, 2020, each of which is incorporated by reference herein in its entirety.

TECHNICAL FIELD

Various aspects of the disclosure relate generally to medical systems, devices, and related methods. At least certain examples of the disclosure relate to systems, devices, and related methods for indexing and controlling a position of one or more medical devices within a patient during a procedure, among other aspects.

BACKGROUND

Technological developments have given users of medical systems, devices, and methods, the ability to conduct increasingly complex procedures on subjects. One challenge in the field of minimally invasive surgeries such as endoscopy, laparoscopy, and thoracoscopy, among other surgical procedures, is associated with providing control of medical devices with respect to an orientation and position of such devices during a procedure. Placement of such medical devices within a patient may be difficult. Additionally, maintaining a desired position of a device is unreliable. The limitations on medical devices that facilitate access of other devices into a patient for placement may prolong the procedure, limit its effectiveness, and/or cause injury to the patient due to device failure or breakage.

SUMMARY

Aspects of the disclosure relate to, among other things, systems, devices, and methods for accessing a target treatment site with a medical apparatus having features that facilitate positioning of the apparatus, among other aspects. Each of the aspects disclosed herein may include one or more of the features described in connection with any of the other disclosed aspects.

According to an example, a medical device includes a sheath, a tool within the sheath and movable relative to the sheath, and a handle including a rotation assembly configured to rotate the tool relative to the sheath in response to rotation of the rotation assembly relative to a portion of the handle. The rotation assembly rotates the tool relative to the sheath at predefined angular intervals and inhibits movement at each of the predefined angular intervals.

Any of the medical devices described herein may have any of the following features. The rotation assembly maintains the tool in the at least one of the predefined angular intervals to fix the tool relative to the sheath. The rotation assembly releases the tool from the at least one of the predefined angular intervals in response to predetermined rotational force applied to the rotation assembly. The rotation assembly generates at least one of a tactile, audible, or visual feedback as the rotation assembly rotates between the predefined angular intervals. The rotation assembly includes a shaft having a plurality of ridges that circumferentially alternate with a plurality of recesses. The handle includes one or more arms. Each of the one or more arms is configured to engage the plurality of ridges and the plurality of recesses. The rotation assembly inhibits rotational movement between the rotation assembly and the portion of the handle, when a first arm of the one or more arms is positioned in a first recess of the plurality of recesses. While the first arm is positioned in the first recess, application of a rotational force onto the rotation assembly relative to the portion of the handle causes the first arm to exit the first recess, and causes the first arm to be positioned in a second recess circumferentially adjacent to the first recess. The one or more arms includes a plurality of arms extending radially inward into a lumen of the handle. Each of the plurality of arms is offset from each of the other plurality of arms. The rotation assembly includes a plurality of recesses or apertures disposed in an outer surface of the rotation assembly. The handle includes one or more detents configured to engage the plurality of recesses or apertures. The rotation assembly inhibits rotational movement between the rotation assembly and the portion of the handle, when a first detent of the one or more detents is positioned in a first recess or aperture of the plurality of recesses or apertures. The first detent includes a compressible portion. While the first detent is positioned in the first recess or aperture, application of a rotational force to the rotation assembly relative to the portion of the handle causes the first detent to compress and exit the first recess, and causes the first detent to be positioned in a second recess or aperture circumferentially adjacent to the first recess or aperture. The rotation assembly includes a distally-facing flange, wherein a protrusion extends distally from the distally-facing flange. The handle includes a proximally-facing flange having a plurality of circumferentially spaced apart recesses or apertures. The protrusion is configured to be received by each of the plurality of recesses or apertures, such that when the protrusion is received by one of the plurality of recesses or apertures, rotational movement between the rotating member and the portion of the handle is inhibited. The medical device further including a deformable member disposed proximally of the distally-facing flange. The deformable member biases the distally-facing flange toward the proximally-facing flange. While the protrusion is positioned in a first recess or aperture, application of a rotational force to the rotation assembly relative to the portion of the handle causes the deformable member to compress, causes the protrusion to exit the first recess or aperture, and causes the protrusion to be positioned in a second recess or aperture circumferentially adjacent to the first recess or aperture. The protrusion includes a compressible portion. While the protrusion is positioned in the first recess or aperture, application of a rotational force to the rotation assembly relative to the portion of the handle causes the protrusion to compress and exit the first recess or aperture, and causes the protrusion to be positioned in a second recess or aperture circumferentially adjacent to the first recess or aperture. The handle includes a plurality of protrusions and a plurality of recesses. The plurality of protrusions and the plurality of recesses alternate with one another. The rotation assembly includes a compressible member. The compressible member is configured to be received by each of the plurality of recesses, such that when the protrusion is received by one of the plurality of recesses, rotational movement between the rotation assembly and the portion of the handle is inhibited. The rotation assembly includes a flange, the flange having a slot enclosed by the flange. The compressible member includes a periphery of the flange defining at least a portion of the slot. While the compressible member is positioned in a first recess, application of a rotational force to the rotation assembly relative to the portion of the handle causes the compressible member to compress radially inward while reducing a volume of the slot, causes the compressible member to exit the first recess, and causes the compressible member to be positioned in a second recess circumferentially adjacent to the first recess or aperture.

According to another example, a medical device includes a handle including a rotation assembly that is movable relative to a remainder of the handle, a sheath extending from the handle, and a tool within the sheath and movable relative to the sheath. The rotation assembly rotates the tool to a plurality of predefined angular positions relative to the sheath in response to rotation of the rotation assembly relative to at least a portion of the handle. The rotation assembly provides at least one of a tactile feedback or audible feedback to a user as the rotation assembly rotates from one of the plurality of predefined angular positions to another of the plurality of predefined angular positions.

Any of the medical devices described herein may have any of the following features. The rotation assembly maintains the tool in the at least one of the predefined angular positions to fix the tool relative to the sheath. The rotation assembly releases the tool from the at least one of the predefined angular positions in response to predetermined rotational force applied to the rotation assembly. The rotation assembly generates at least one of a tactile, audible, or visual feedback as the rotation assembly rotates between the predefined angular positions. The rotation assembly includes a shaft having a plurality of ridges that circumferentially alternate with a plurality of recesses. The handle includes one or more arms. Each of the one or more arms is configured to engage the plurality of ridges and the plurality of recesses. The rotation assembly inhibits rotational movement between the rotation assembly and the portion of the handle, when a first arm of the one or more arms is positioned in a first recess of the plurality of recesses.

According to another example, a method of rotating a tool relative to a sheath to a plurality of predefined angular positions includes rotating an assembly relative to a handle away from a first predefined angular position to a second predefine angular position. The method includes generating a first indexing feedback at the rotation assembly in response to rotating the rotation assembly out of the first predefined angular interval, and generating a second indexing feedback at the rotation assembly in response to rotating the rotation assembly into the second predefined angular position. The first predefined angular position is configured to maintain the tool at a first fixed orientation relative to the sheath, and the second predefined angular position is configured to maintain the tool at a second fixed orientation relative to the sheath.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1A:
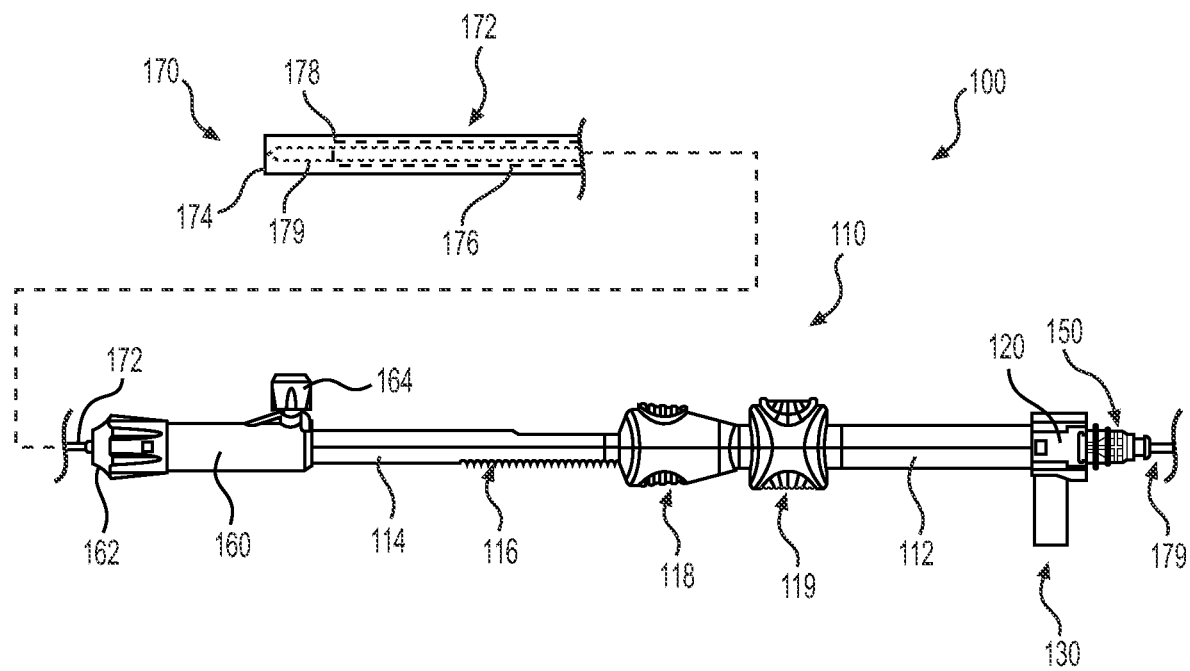
FIG. 1A is a side view of an exemplary medical system including a medical device and a medical instrument, with the medical device having a rotation assembly, according to aspects of this disclosure.

Examples of the disclosure include systems, devices, and methods for indexing a position and/or orientation of multiple components of a medical instrument at a target site within the body, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to facilitate control of a position and orientation of tools/devices of a medical instrument at a target treatment site by providing one or more mechanisms and/or assemblies for indexing movement of said tools/devices. For example, some examples combine a rotation assembly on a medical device for selective control and/or manipulation of components of a medical instrument received within the medical device to a plurality of predefined angular intervals/positions. The rotation assembly may be configured to control the radial orientation of a distal end of a medical instrument. The medical device may include a body that defines a lumen configured to receive the medical instrument therein, and a rotation assembly coupled to the medical instrument for moving the medical instrument within the lumen of the body. The medical instrument may include a sheath and a tool disposed within the sheath, such as, for example, an access cannula. The rotation assembly may be positioned external to the body and coupled to the tool of the medical instrument within the lumen, such that a position and orientation of the tool may be indexed relative to the body in response to actuation of the rotation assembly. The rotation assembly of the medical device may further provide selective control and/or manipulation of components of the medical device to a plurality of predefined angular intervals/positions.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). The device and related methods may be used laparoscopically or endoscopically, or in any other open or minimally invasive procedure, including thorascopic and ENT procedures. Reference will now be made in detail to examples of the disclosure described above and illustrated in the accompanying drawings. Wherever possible, the same reference numbers will be used throughout the drawings to refer to the same or like parts.

FIG. 1A shows a schematic depiction of an exemplary medical system 100 in accordance with an example of this disclosure. The medical system 100 may include a handle 110 and a medical instrument 170. In the example, the handle 110 includes an outer body 112 and an inner body 114, with the outer body 112 having a longitudinal length and defining a lumen which is sized, shaped, and configured to receive the inner body 114. As described in greater detail herein, the outer body 112 is configured to move relative to the inner body 114, and vice versa, the inner body 114 is configured to move relative to the outer body 112. The inner body 114 of the handle 110 has a longitudinal length, and defines a lumen which is sized, shaped, and configured to receive the medical instrument 170.

In the example, the inner body 114 includes a rack portion having a plurality of teeth 116 extending along an exterior of the inner body 114. The plurality of teeth 116 extend along at least a portion of a longitudinal length of the inner body 114 (up to an entirety of the longitudinal length) that corresponds to a range of motion of the outer body 112 relative to the inner body 114. Accordingly, it should be understood that the rack portion including the plurality of teeth 116 may extend along various other suitable lengths and/or surfaces of the inner body 114 than that shown and described herein without departing from a scope of this disclosure. The handle 110 may further include a cap cover 120, an end cap 130, and a rotation assembly 150 disposed on and/or coupled to the outer body 112. The cap cover 120 of the handle 110 may be positioned at a proximal end of the outer body 112 and, when secured thereto, is configured to enclose a lumen of the outer body 112 between the cap cover 120 and the outer body 112. The end cap 130 and the rotation assembly 150 extend from and/or are coupled to the cap cover 120. As described in greater detail herein, the cap cover 120, the end cap 130, and the rotation assembly 150 of the handle 110 may have various suitable configurations and/or arrangements relative to one another and to the handle 110.

Figure 1B:
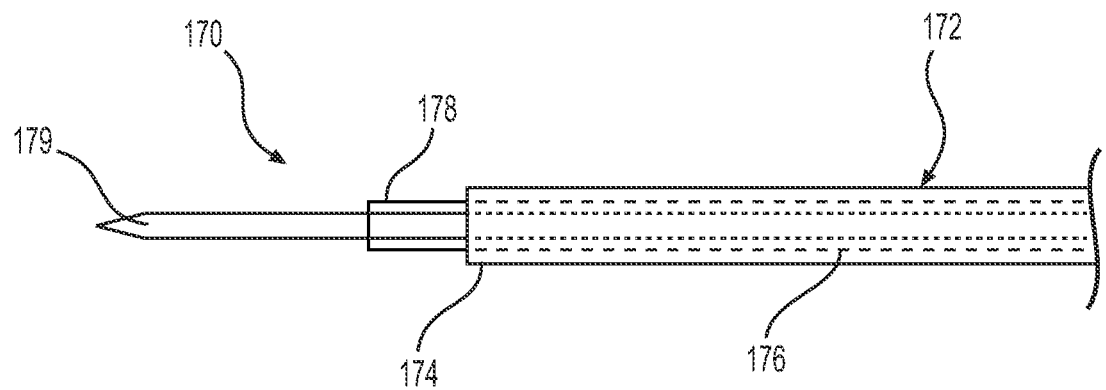
FIG. 1B is a cross-sectional side view of the medical instrument of FIG. 1, with the medical instrument including a needle in an extended state, according to aspects of this disclosure.

Further, the medical instrument 170 of the medical system 100 may include a catheter having a sheath 172, a cannula 176, and a needle 179. The cannula 176 may be disposed within a lumen of the sheath 172, and the needle 179 may be disposed within a lumen of the cannula 176, and may extend at least partially outward from the tip 178 of the cannula 176. In the example, a position, orientation, and/or configuration of the needle 179 relative to the cannula 176 is fixed such that a distal end of the needle 179 is maintained at an extended position relative to the tip 178 of the cannula 176. The sheath 172 includes a tip 174 and has a longitudinal length defined by the distance between the tip 174 and a proximal end of the sheath 172 (not shown). The cannula 176 of the medical instrument 170 includes a tip 178 and has a longitudinal length defined by the distance between the tip 178 and a proximal end of the cannula 176 (not shown). As described in greater detail herein, one or more components of the handle 110 may be configured and operable to position the medical instrument 170 relative to a target treatment site within a patient (e.g., patient anatomy). For example, the medical instrument 170 may be operable to puncture a target treatment site with the needle 179, when the needle 179 is extended distally from the tip 174, as shown in FIG. 1B.

Still referring to FIG. 1A, in some examples, the medical instrument 170 may be operable to facilitate access of one or more tools and/or devices to a target treatment site with the cannula 176, including and/or in addition to the needle 179. In this instance, upon removal of the needle 179 from a lumen of the cannula 176, one or more additional tools and/or devices may be received through a lumen of the cannula 176 and extended outwardly and distally therefrom via the tip 178 of the cannula 176. In some examples, the cannula 176 may be configured and operable to deform in response to the needle 179 being at least partially retracted from the tip 178 of the cannula 176. Additionally and/or alternatively, in other examples the cannula 176 may be configured and operable to deform in response to the tip 178 of the cannula 176 being extended outwardly and distally from the tip 174 of the sheath 172, or vice versa, the tip 174 of the sheath 172 being extended proximally relative to the tip 178 of the cannula 178).

Figure 1C:
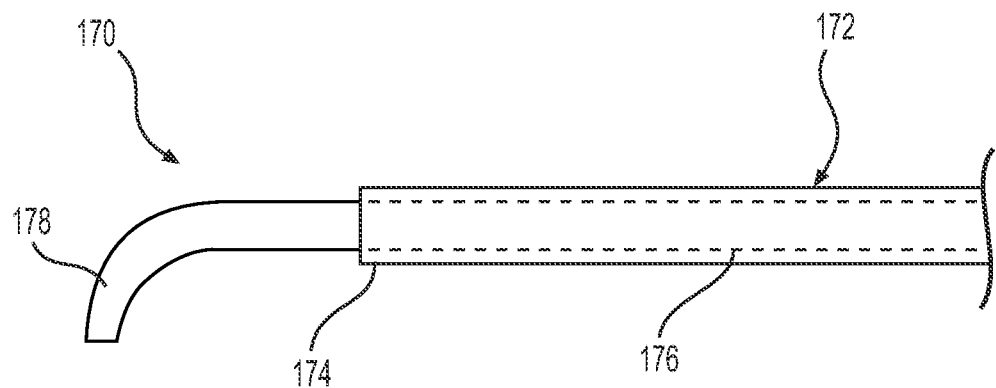
FIG. 1C is a cross-sectional side view of the medical instrument of FIG. 1, with the medical instrument including a cannula in an extended state, according to aspects of this disclosure.

As shown in FIG. 1C, the tip 178 of the cannula 176 may be configured and operable to conform to a predetermined shape and/or configuration (e.g., J-shaped) when the needle 179 is omitted and/or the tip 178 is extended out from a lumen of the sheath 172. It should be appreciated that retraction of the needle 179 from the cannula 178, and/or extension of the tip 178 from a lumen of the sheath 172, may remove forces applied to the cannula 176 and restraining the tip 178 to a shape and/or configuration, such as, for example, a linear profile as shown in FIGS. 1A-1B. As described in further detail herein, a rotation assembly of the handle 110 may be configured and operable to control a positioning of the J-shaped tip 178 of the cannula 176 during a procedure.

Further, in some examples, the medical instrument 170 may be operable to electrosurgically dilate a target treatment site with the sheath 172. In this instance, the sheath 172 includes an electrosurgical sheath and the tip 174 includes an electrosurgical tip. It should be understood that, in other examples, the medical instrument 170 may include various other suitable tools, configurations, hypotubes and/or components than those shown and described herein. By way of illustrative example, in some examples the medical instrument 170 may include an electrosurgical end (e.g., cystotome needle) that omits the tip 178, such as, for example, for delivering a stent during a procedure. In other examples the medical instrument 170 omits components configured for electrical activation.

Referring back to FIG. 1A, the handle 110 may further include a first actuator 118 and a second actuator 119 positioned on the outer body 112. In the example, the first actuator 118 and the second actuator 119 are disposed over the outer body 112. The first actuator 118 is secured and/or coupled to the outer body 112 and is configured to move the outer body 112 relative to the inner body 114 in response to actuation of the first actuator 118. In the example, the first actuator 118 is integral with the outer body 112 such that the first actuator 118 forms a unitary structure with the outer body 112. Further, the second actuator 119 is secured and/or coupled to the inner body 114 and is configured to move the inner body 114 relative to the outer body 112 in response to actuation of the second actuator 119. For instance, the second actuator 119 may be coupled to the inner body 114 through the outer body 112, such as, for example, via one or more openings and/or slots (not shown) formed through the outer body 112. The first actuator 118 and the second actuator 119 may be configured and operable in accordance with at least some of the teachings of U.S. App. No. 62/957,553, entitled "Medical Device Locking Assemblies and Methods of Using the Same," filed on Jan. 6, 2020 (later filed as U.S. application Ser. No. 17/137,070, filed Dec. 29, 2020, and published as U.S. Pre-Grant Publication No. 2021/0205012), the disclosure of which is incorporated by reference herein.

The handle 110 further includes a distal housing 160 positioned at a distal end of the inner body 114 opposite of the outer body 112. The distal housing 160 of the handle 110 defines a lumen that is sized, shaped, and configured to receive one or more components of the handle 110 therethrough, such as, for example, at least a portion of the inner body 120, the medical instrument 170, and the like. The distal housing 160 of the handle 110 may further include a housing tip 162 and a screw (fastener) 164. In the example, the housing tip 162 includes an opening that is sized and shaped to facilitate an exit of the medical instrument 170 from a lumen of the distal housing 160 and/or the inner body 114. The screw 164 is configured to engage an exterior surface of the inner body 114 within a lumen of the distal housing 160 to securely couple the inner body 114 to the distal housing 160. In this instance, the screw 164 is movable (e.g., rotatable) relative to the distal housing 160 to selectively engage and/or disengage the inner body 114 received therein. It should be appreciated that various other suitable fastening elements, clamps, pins, and the like are also contemplated without departing from a scope of this disclosure.

The following description provides various examples of the cap cover 120, the end cap 130, and the rotation assembly 150 shown and described above. Each of the exemplary cap covers 120, end caps 130, and/or rotation assemblies 150 noted herein may be used with the handle 110 and the medical instrument 170 described above, and in any of the various procedures described herein. Accordingly, it should be understood that any of the cap covers 120, the end caps 130, and/or the rotation assemblies 150 shown and described herein (see FIGS. 2-12) may be readily incorporated into the medical system 100 detailed above and shown in FIG. 1A.

Figure 2:
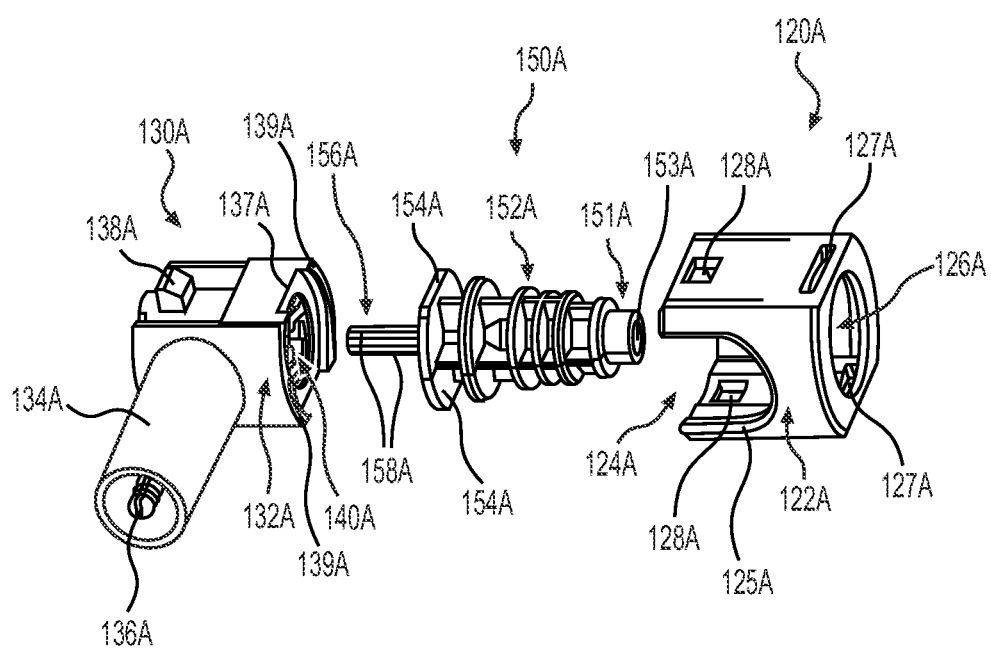
FIG. 2 is an exploded view of the rotation assembly of FIG. 1, according to aspects of this disclosure.

Referring now to FIG. 2, an example of a cap cover 120A, an end cap 130A, and a rotation assembly 150A is shown and described herein. In the example, the cap cover 120A includes a body 122A defined by a distal opening 124A and a proximal opening 126A. As described further herein, the distal opening 124A of the body 122A is sized, shaped, and configured to at least partially receive the end cap 130A and/or the rotation assembly 150A therethrough. Further, the proximal opening 126A of the body 122A is sized, shaped, and configured to receive the rotation assembly 150A therethrough. The body 122A of the cap cover 120A further includes a recess 125A formed along a sidewall of the body 122A between the distal opening 124A and the proximal opening 126A. As described further herein, the recess 125A is sized and shaped to receive one or more components of the end cap 130A when the cap cover 120A is coupled thereto (e.g., a pin housing 134A). The cap cover 120A may include one or more slots 127A formed along one or more sidewalls of the body 122A. The one or more slots 127A may extend along an axis transverse (e.g., substantially perpendicular) to a longitudinal axis of the handle 110. The cap cover 120A includes a pair of slots 127A formed through a pair of sidewalls of the body 122A and positioned relatively adjacent to the proximal opening 126A.

Additionally, the cap cover 120A may include one or more apertures 128A formed along one or more sidewalls of the body 122A. The cap cover 120A includes a pair of apertures 128A formed through a pair of sidewalls of the body 122A and positioned relatively adjacent to the distal opening 124A. In the example, the pair of slots 127A and the pair of apertures 128A of the cap cover 120A are formed along the same sidewalls of the body 122A, however, it should be understood that the slots 127A and/or the apertures 128A may be positioned along various other walls and/or surfaces of the body 122A of the cap cover 120A without departing from a scope of this disclosure. For example, the same sidewall(s) of the body 122A may include the slot 127A and the aperture 128A. It should further be understood that, in other examples, the cap cover 120A may include additional and/or fewer slots 127A and apertures 128A than those shown and described herein.

Still referring to FIG. 2, the end cap 130A includes a central body 132A and a pin housing 134A extending radially outward from the central body 132A. The pin housing 134A may be transverse (e.g., substantially perpendicular) to a longitudinal axis of the central body 132A of the end cap 130A. As noted above, the pin housing 134A extends outwardly from the body 122A of the end cap 130A through the recess 125A when the end cap 130A is coupled to the cap cover 120A. The pin housing 134A of the end cap 130A includes an active pin 136A disposed therein such that the pin housing 134A encloses the active pin (connector) 136A. In the example, the active pin 136A may be operable to establish communication with the medical instrument 170 when the end cap 130A is coupled to the outer body 112 and the medical instrument 170 is disposed within the inner body 120. For example, the active pin 136A may be communicatively couple to one or more components of the medical instrument 170, such as, for example, the sheath 172 (e.g., an electrosurgical sheath comprising an electrically conductive material). In this instance, the active pin 136A is operable to establish electrosurgical connection between the sheath 172 of the medical instrument 170 and an ancillary device, such as, for example, an electrosurgical generator (not shown) operable to generate high frequency electric or RF current.

The body 132A of the end cap 130A may include one or more components that are configured and operable to engage corresponding components of the cap cover 120A to couple the end cap 130A to the cap cover 120A. For example, in the example, the end cap 130A may include one or more protrusions 138A extending outwardly from one or more sidewalls of the central body 132A and positioned relatively adjacent to a distal end of the body 132A. It should be understood that a quantity of the protrusions 138A included on the body 132A of the end cap 130A corresponds to a quantity of the apertures 128A included on the body 122A of the cap cover 120A. In the example, the end cap 130A includes a pair of protrusions 138A in accordance with the pair of apertures 128A on the cap cover 120A. In this instance, each of the pair of protrusions 138A may be sized and shaped to correspond with a size and shape of the aperture 128A such that the pair of apertures 128A are configured to receive the pair of protrusions 138A therein, respectively, to couple the cap cover 120A to the end cap 130A. In other examples, the protrusions 138A may include various other suitable shapes, sizes, and/or configurations than those shown and described herein. Furthermore, additional and/or fewer protrusions 138A may be included on the body 132A of the end cap 130A without departing from a scope of this disclosure.

Still referring to FIG. 2, the end cap 130A may include one or more ledges 139A disposed along a proximal end of the body 132A. The one or more ledges 139A may be disposed between, and defined by, one or more recesses 137A disposed along a proximal end of the body 132A. In the example, the end cap 130A includes recesses 137A formed and defined between an adjacent pair of ledges 139A. As described further herein, the ledges 139A of the end cap 130A are sized and shaped in accordance with one or more components of the rotation assembly 150A (e.g., a distal flange 154A) to facilitate an alignment and/or engagement of the rotation assembly 150A to a proximal end of the end cap 130A. The end cap 130A further includes an engagement interface 140A positioned along a proximal end of the body 132A. As described in further detail herein, the engagement interface 140A may include one or more components that are configured and operable to engage corresponding components of the rotation assembly 150A to couple the end cap 130A to the rotation assembly 150A.

The rotation assembly 150A may include a body 152A defined by a distal flange 154A and a proximal end 151A. In the example, the body 152A of the rotation assembly 150A may include one or more features disposed along an exterior of the rotation assembly 150A to facilitate a manual manipulation of the rotation assembly 150A. By way of example only, the body 152A of the rotation assembly 150A may include one or more protrusions, recesses, flanges, tabs, and like surface features for providing ease to grasp the body 152A by a user of the medical system 100. The body 152A is further sized and shaped to be received through the distal opening 124A and the proximal opening 126A of the cap cover 120A when the rotation assembly 150A is inserted into the cap cover 120A. It should be appreciated that the distal flange 154A of the rotation assembly 150A is sized relatively greater than at least the proximal opening 126A to inhibit removal of the rotation assembly 150A from the cap cover 120A via the proximal opening 126A during use of the medical system 100.

Still referring to FIG. 2, the distal flange 154A extends radially outward from the body 152A, for example, the distal flange 154A extends about an outer perimeter of the body 152A. In some examples, the distal flange 154A may include one or more flat edges and/or one or more curved edges. In the example shown and described herein, the distal flange 154A includes a pair of flat edges each disposed between a pair of curved edges. The pair of curved edges of the distal flange 154A are sized and shaped in accordance with a size and shape of the ledges 139A of the end cap 130A. Accordingly, it should be appreciated that the distal flange 154A is configured to be received by and/or between the pair of ledges 139A of the end cap 130A in response to moving a distal end of the rotation assembly 150A toward a proximal end of the end cap 130A. In some examples, the one or more ledges 139A of the end cap 130A may be operable to snap onto and/or interlock with the distal ledge 154A of the rotation assembly 150A to couple the rotation assembly 150A to the end cap 130A.

It should be appreciated that the slots 127A on the body 122A of the cap cover 120A and the recesses 137A on the body 132A of the end cap 130A are sized, shaped, and configured to receive the curved edges of the distal flange 154A when the rotation assembly 150A is received between and rotated relative to the cap cover 120A and the end cap 130A. In other words, the slots 127A and the recesses 137A are operable to accommodate the curved edges of the distal flange 154A when the rotation assembly 150A is rotated such that the curved edges 154A are aligned with the slots 127A and the recesses 137A, respectively.

Still referring to FIG. 2, the rotation assembly 150A further includes a distal shaft 156A extending outwardly from the distal flange 154A. The distal shaft 156A extends distally from the distal shaft 156A away from the body 152A and the proximal end 151A. The distal shaft 156A may include one or more ridges 158A disposed along a longitudinal length of the distal shaft 156A. In the example, the distal shaft 156A includes a plurality of ridges 158A extending radially outward from an exterior of the distal shaft 156A. The plurality of ridges 158A of the distal shaft 156A may be defined by at least one recess formed between a pair of adjacent ridges 158A. As described in further detail herein, the ridges 158A on the distal shaft 156A are configured to engage one or more components of the engagement interface 140A on the end cap 130A (e.g., a flex arm 142A) to couple the rotation assembly 150A to the end cap 130A and provide tactile feedback during use (e.g., rotation of the rotation assembly 150A). The proximal end 151A of the rotation assembly 150A includes a proximal opening 153A that facilitates access to a lumen of the rotation assembly 150A. It should be understood that a lumen of the rotation assembly 150A may extend through the body 152A from the proximal opening 153A to a distal opening positioned at a terminal distalmost end of the distal shaft 156A (see FIG. 3). As described above, a lumen of the rotation assembly 150A is sized, shaped, and configured to receive one or more tools and/or devices therethrough, such as, for example, the needle 179 of the medical instrument 170.

Figure 3:
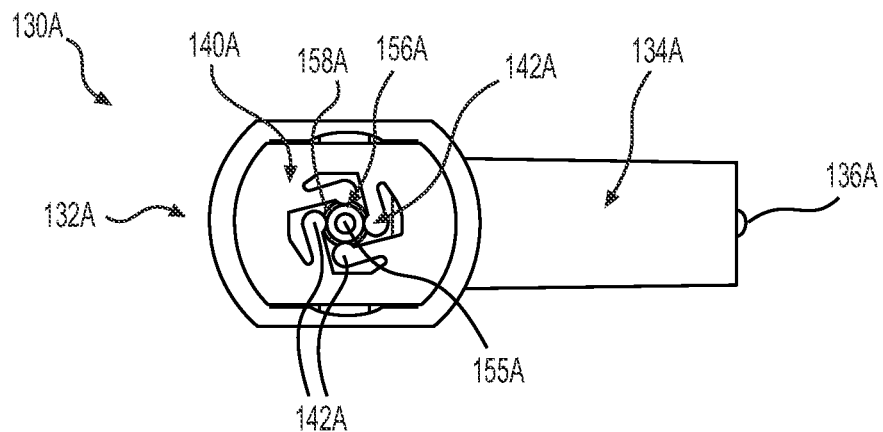
FIG. 3 is a bottom view of the rotation assembly of FIG. 1, according to aspects of this disclosure.

Referring now to FIG. 3, the distal shaft 156A of the rotation assembly 150A may be received in the body 132A of the end cap 130A through a proximal end of the end cap 130A. The engagement interface 140A of the end cap 130A may include one or more flex arms 142A extending from an inner circumferential surface, radially inward into a lumen of the end cap 130. The one or more flex arms 142A may be circumferentially adjacent to one another and offset relative to an adjacent flex arm 142A. In some examples, the one or more flex arms 142A extend along an axis that is offset from a longitudinal axis of the engagement interface 140 (e.g., does not intersect a radial center of a lumen of the engagement interface 140A). In other words, the one or more flex arms 142A do not extend toward a radial center of the engagement interface 140A.

In the example, the engagement interface 140A includes four flex arms 142A, however, it should be appreciated that in other examples, the engagement interface 140A may include additional and/or fewer flex arms 142A. The flex arms 142A are configured to engage the one or more ridges 158A on the distal shaft 156A of the rotation assembly 150A when the rotation assembly 150A is received within the end cap 130A. In some examples, the flex arms 142A may include an abutment feature at a distal end of the flex arm 142A that is configured and operable to engage the one or more ridges 158A of the distal shaft 158A, such as, for example, a protrusion, a rounded/circular tip, a curved surface, and the like. Accordingly, the flex arms 142A are operable to at least partially couple the rotation assembly 150A to the end cap 130A in response to engaging the one or more ridges 158A on the distal shaft 156A. It should be appreciated that the flex arms 142A of the end cap 130A extend into a lumen of the body 132A at an angular array and are flexibly deformable such that the flex arms 142A are configured to deform in response to receiving a radial force applied thereto.

Figure 10:
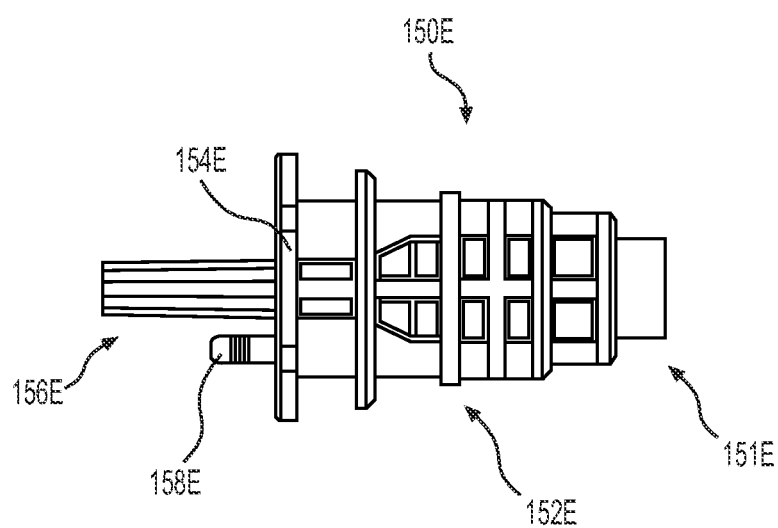
FIG. 10 is a side view of another exemplary rotation assembly of the medical device of FIG. 1, according to aspects of this disclosure.

According to an exemplary method of using the cap cover 120A, the end cap 130A, and the rotation assembly 150A with the medical system 100 during a procedure, the medical system 100 may initially be inserted into a patient and maneuvered such that the medical instrument 170 received within the handle 110 is positioned adjacent to a target treatment site. At least the cannula 176 of the medical instrument 170 is secured to the rotation assembly 150A such that rotation of the rotation assembly 150A relative to the cap cover 120A, the end cap 130, and/or the handle 110 provides a rotation of the cannula 176 within a lumen of the outer body 112 and the inner body 114. Thus, the rotation assembly 150A may control a radial orientation of the tip 178 of the cannula. In examples where the tip 178 includes a predetermined shape and/or configuration, such as, for example, a J-shaped tip 178 as shown in FIG. 10, rotation of the rotation assembly 150A provides positional and/or directional control of the J-shaped tip 178. Accordingly, a user may actuate the rotation assembly 150A at a proximal end of the medical system 100 to rotate the cannula 176 and the tip 178 of the cannula 176 near the target treatment site. With the needle 179 received within the cannula 176, it should be appreciated that actuation of the rotation assembly 150A may provide a simultaneous rotation of the needle 179 with the cannula 176. In some examples, the needle 179 may be removed from within a lumen of the cannula 176 such that actuation of the rotation assembly 150A may provide rotation of the cannula 176 and/or other devices/instruments disposed within the cannula 176.

With the distal shaft 156A of the rotation assembly 150A extending through a lumen of the end cap 130A, the flex arms 142A of the end cap 130A may flex outwardly as the distal shaft 156A of the rotation assembly 150A rotates therein. The ridges 158A on the distal shaft 156A may abut against the flex arms 142A thereby applying an outward radial force onto the flex arms 142A. In this instance, the ridges 158A may cause each of the flex arms 142A to bend at least partially away from the distal shaft 156A until becoming aligned with a recess formed between a pair of adjacent ridges 158A. Receipt of a portion of the flex arms 142A in the recesses on the distal shaft 156A may at least partially fix a radial orientation of the rotation assembly 150A relative to the cap cover 120A, the end cap 130A, and the handle 110. It should be appreciated that the flex arms 142A may partially inhibit further rotation of the rotation assembly 150A when received within a recess on the distal shaft 156A (for example, until the rotation assembly 150A is rotated again by a user).

In the example, the rotation assembly 150A is configured to generate an indexing feedback in response to rotating the rotation assembly 150A relative to the cap cover 120A, the end cap 130A, and/or the handle 110. For example, a user of the medical system 100 may experience a tactile, audible and/or visual feedback at the body 152A of the rotation assembly 150A when the flex arms 142A of the end cap 130A are received within the recesses between an adjacent pair of ridges 158A and/or when rotating the rotation assembly 150A. In this instance, a user of the medical system 100 may incrementally index a position (e.g., orientation) of the medical instrument 170, for example, the cannula 176 and the needle 179 (when disposed within the cannula 176), relative to the handle 110 by receiving the indexing feedback.

It should be appreciated that the recesses formed between adjacent ridges 158A along the distal shaft 156A form a plurality of predefined angular intervals that the rotation assembly 150A (and the medical instrument 170) may be positioned at. Accordingly, a quantity of the recesses and/or the ridges 158A included along the distal shaft 156A may determine a quantity of the predefined angular intervals formed by the rotation assembly 150A. Further, the ridges 158A on the distal shaft 156A are configured to inhibit movement of the rotation assembly 150A at each of the plurality of predefined angular intervals by engaging the flex arms 142A with adjacent pairs of ridges 158A. The flex arms 142A may provide a force for maintaining the rotation assembly 150A in at least one of the predefined angular intervals. This force may be overcome to allow movement of the rotation assembly 150A and the cannula 176 relative to the handle 110, by applying a rotational force onto the body 152A greater than the force applied by the flex arms 142A.

Figure 4:
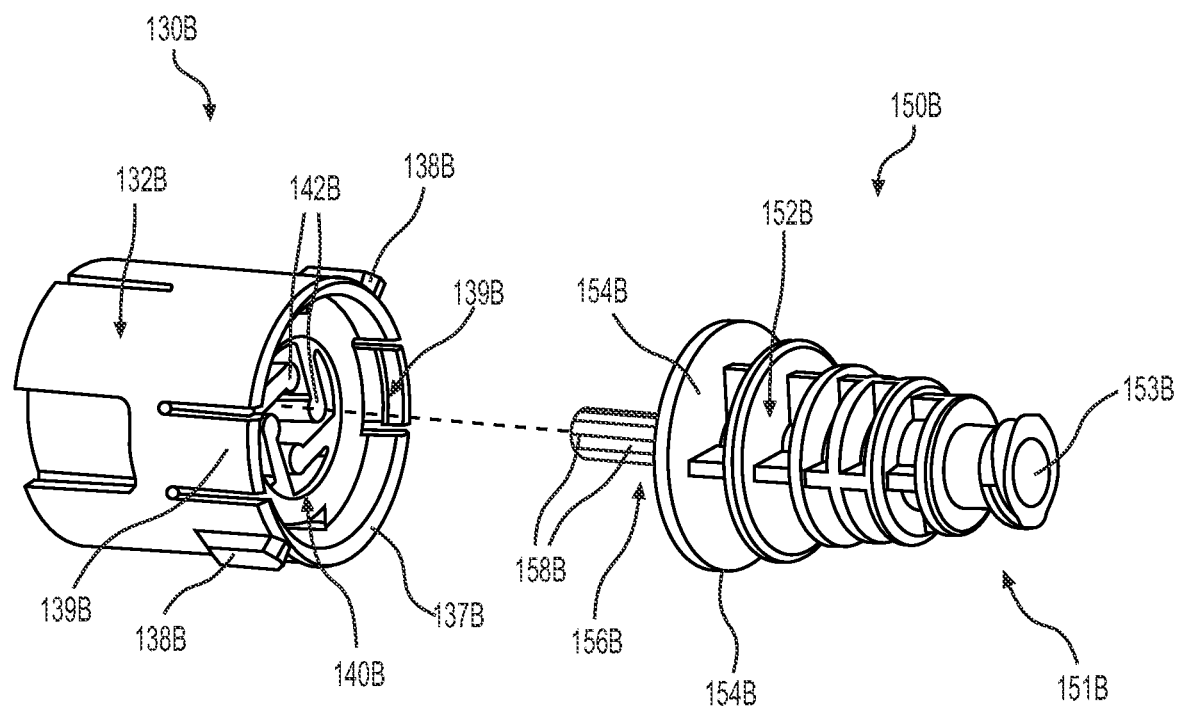
FIG. 4 is an exploded view of another exemplary rotation assembly of the medical device of FIG. 1, according to aspects of this disclosure.

Referring now to FIG. 4, an example of an end cap 130B and a rotation assembly 150B is shown and described herein. It should be understood that the end cap 130B and the rotation assembly 150B of the example may be incorporated with the cap cover 120A shown and described above. It should further be understood that, except as otherwise explicitly noted herein, the end cap 130B and the rotation assembly 150B may be configured and operable similar to the end cap 130A and the rotation assembly 150A described above, respectively, such that corresponding numerals are used to identify similar features. For example, the rotation assembly 150B may include a body 152B defined by a proximal end 151B and a distal flange 154B, with the proximal end 151B including a proximal opening 153B that facilitates access to a lumen of the rotation assembly 150B.

It should be understood that the body 152B of the rotation assembly 150B may include one or more luer features, such as, for example, at and/or adjacent to the proximal opening 153B, as shown in FIG. 4. In this instance, the luer feature of the rotation assembly 150B may be configured to allow attachment of a medical instrument (e.g., a syringe) to the proximal opening 153B of the rotation assembly 150B, thereby facilitating fluid communication between a lumen of the rotation assembly 150B and the medical instrument. Further, the rotation assembly 150B includes a distal shaft 156B extending distally from the distal flange 154B and defining at least a distal portion of the lumen of the rotation assembly 150B. The rotation assembly 150B differs from the rotation assembly 150A described above in that the distal flange 154B is defined by a single continuous curved edge extending about an outer perimeter of the body 152B.

The end cap 130B may include a body 132B having one or more alignment features 138B disposed along an exterior of the body 132B. In the example, the end cap 130B includes a pair of alignment features 138B, however, it should be understood that the end cap 130B may include additional and/or fewer alignment features 138B without departing from a scope of the disclosure. The pair of alignment features 138B are configured to engage a corresponding feature of one or more other components of the medical device 100 to facilitate an alignment and/or engagement of the end cap 130B to the component of the medical device 100, such as, for example, a rotation assembly cover (not shown) configured to enclose the rotation assembly 150A therein, the cap cover 120A, and/or the like. For example, the rotation assembly cover may be a component of the needle 179, and the alignment features 138B may interface with the rotation assembly cover as a rotational stop.

Still referring to FIG. 4, the end cap 130B may further include a ledge 137B and one or more locks 139B extending about a proximal end of the body 132B. In the example, the end cap 130B includes a pair of locks 139B, with each of the locks 139B disposed circumferentially adjacent the ledge 137B at a proximal end of the body 132B. The ledge 137B is sized and shaped in accordance with a profile of the distal flange 154B of the rotation assembly 150B such that the ledge 137B is configured to receive the distal flange 154B therein. The pair of locks 139B are flexibly movable relative to the ledge 137B and are configured to engage the distal flange 154B to couple the end cap 130B to the rotation assembly 150B in response to the distal flange 154B being received against the ledge 137B. In some examples, the pair of locks 139B may include a protrusion extending radially inward relative to the ledge 137B such that the protrusion of the lock 139B is operable to abut against the distal flange 154B to secure the rotation assembly 150B to the end cap 130B.

The end cap 130B further includes an engagement interface 140B at a proximal end of the body 132B that has one or more flex arms 142B extending inwardly into a lumen of the end cap 130B. In the example, the flex arms 142B of the engagement interface 140B are substantially similar to the flex arms 142A of the engagement interface 140A on the end cap 130A shown and described above. The distal shaft 156B of the rotation assembly 150B includes one or more ridges 158B and corresponding recesses formed between adjacent pairs of ridges 158B. In the example, the ridges 158B and the distal shaft 156B of the rotation assembly 150B are substantially similar to the ridges 158A and the distal shaft 156A of the rotation assembly 150A shown and described above. Accordingly, the rotation assembly 150B is configured and operable to interact with the end cap 130B as similarly described above with respect to the rotation assembly 150A and the end cap 120A.

Figure 5:
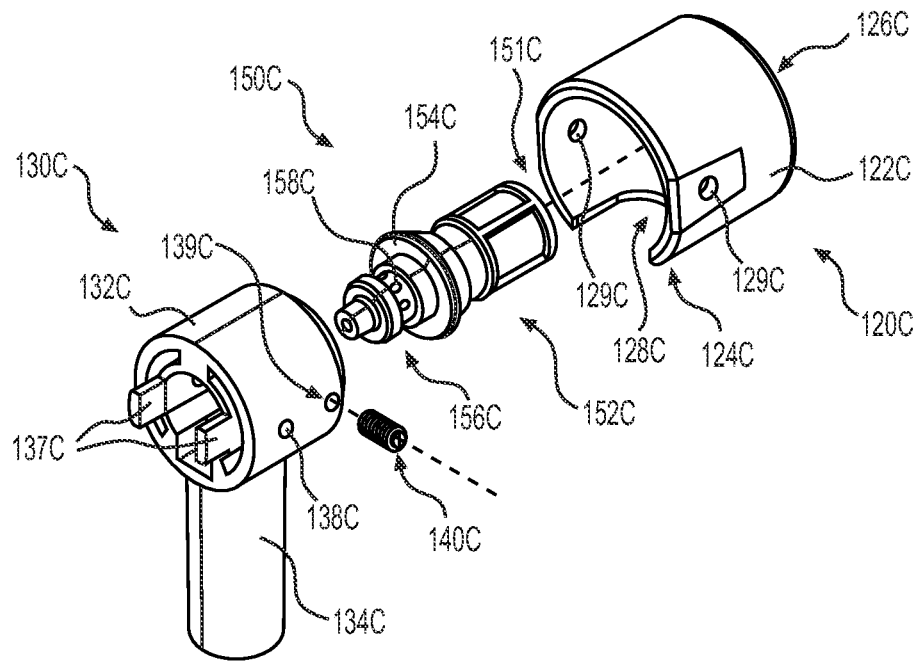
FIG. 5 is an exploded view of another exemplary rotation assembly of the medical device of FIG. 1, according to aspects of this disclosure.

Referring now to FIG. 5, an example of a cap cover 120C, an end cap 130C, and a rotation assembly 150C is shown and described herein. It should be understood that, except as otherwise explicitly noted herein, the cap cover 120C, the end cap 130C, and the rotation assembly 150C may be configured and operable similar to the cap cover 120A, the end cap 130A, and the rotation assembly 150A described above, respectively, such that corresponding numerals are used to identify similar features. For example, the rotation assembly 150C may include a body 152C defined by a proximal end 151C and a distal flange 154C, with the proximal end 151C including a proximal opening 153C (FIG. 6) that facilitates access to a lumen of the rotation assembly 150C. Further, the rotation assembly 150C includes a distal shaft 156C extending distally from the distal flange 154C. The rotation assembly 150C differs from the rotation assembly 150A described above in that the distal shaft 156C includes one or more apertures 158C formed thereon. The distal shaft 156C of the rotation assembly 150C includes a plurality of apertures/recesses 158C extending along an annular array about an exterior of the distal shaft 156C. It should be appreciated that the plurality of apertures/recesses 158C may be spaced from one another along the distal shaft 156C of the rotation assembly 150C at any suitable interval.

The cap cover 120C may include a body 122C defined by a distal opening 124C and a proximal opening 126C. The distal opening 124C is sized, shaped, and configured to receive the rotation assembly 150C and the cap cover 120C therethrough. The body 122C further includes a recess 128C that is sized and shaped to receive one or more components of the end cap 130C therethrough, such as, for example, a pin housing 134C. The body 122C of the cap cover 120C further includes one or more openings 129C through an exterior of the body 122C into a lumen of the body 122C. As described further below, the cap cover 120C includes a pair of openings 129C that are each configured to receive a fastener (not shown) therethrough for coupling the cap cover 120C to another component of the medical system 100, such as, for example, the end cap 130C (FIG. 6).

Still referring to FIG. 5, the end cap 130C may include a body 132C having a pin housing 134C extending outwardly therefrom and one or more engagement tabs 137C extending distally from a distal end of the body 132C. In the example, the end cap 130C includes a pair of engagement tabs 137C extending distally from a distal end of the body 132C, with the engagement tabs 137C disposed about a lumen of the body 132C. It should be understood that the pair of engagement tabs 137C are configured to align and/or engage the end cap 130C to the handle 110 of the medical system 100. For example, the pair of engagement tabs 137C may be operable to engage the outer body 112 of the handle 110 to thereby couple the end cap 130C to the outer body 112.

The end cap 130C may further include one or more openings 138C, 139C formed through an exterior of the body 132C such that the openings 138C, 139C extend into a lumen of the body 132C. The end cap 130C includes a pair of distal openings 138C and a pair of proximal openings 139C, with the distal openings 138C positioned adjacent to a distal end of the body 132C relative to the proximal openings 139C and the proximal openings 139C positioned adjacent to a proximal end of the body 132C relative to the distal openings 138C. As described further below, the pair of distal openings 138C are each configured to receive a fastener (not shown) therethrough for coupling the end cap 130C to another component of the medical system 100, such as, for example, the cap cover 120C (FIG. 6). In the example, the end cap 130C further includes a detent 140C that is sized, shaped, and configured to be received within at least one of the proximal openings 139C. As described in further detail herein, the detent 140C is configured to engage at least one of the plurality of recesses 158C along the distal shaft 156C of the rotation assembly 150C in response to the end cap 130C receiving the rotation assembly 150C therethrough. In some examples, the detent 140C may include a ball and/or protrusion feature coupled to a distal end of a spring and/or biasing mechanism. In this instance, the ball/protrusion at the distal end of the spring may be the portion of the detent 140C received within the recess 158C. In other examples, the detent 140C may include an elastic protrusion that is longitudinally expandable and compressible.

Figure 6:
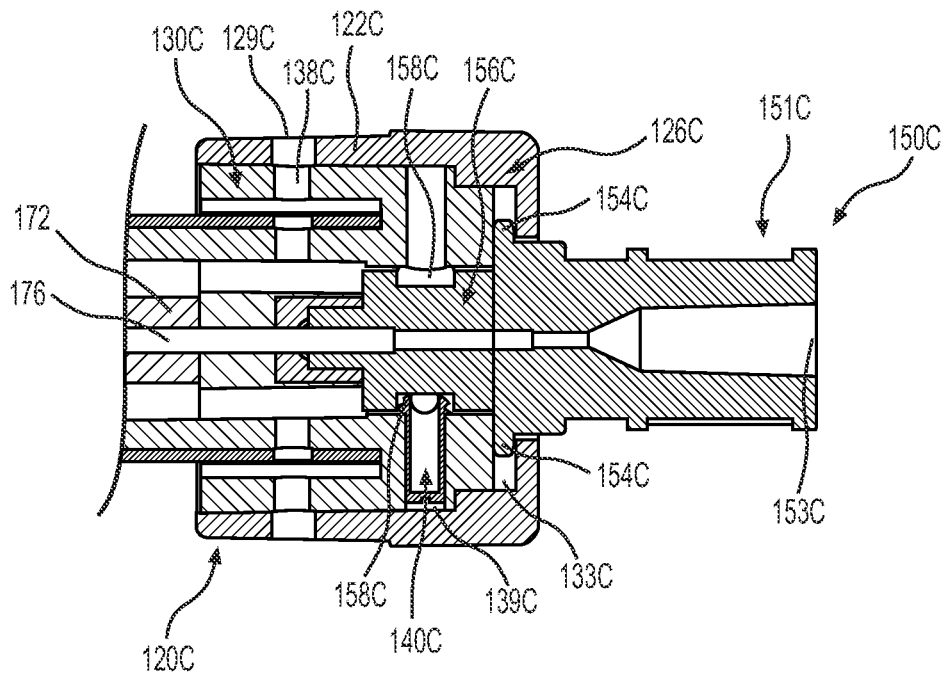
FIG. 6 is a cross-sectional view of the rotation assembly of FIG. 5, according to aspects of this disclosure.

Referring now to FIG. 6, the detent 140C is depicted within the proximal opening 139C and engaged with at least one of the plurality of recesses 158C. In this instance, the detent 140C at least partially maintains the rotation assembly 150C at a fixed radial position (e.g., orientation) relative to the cap cover 120C, the end cap 130C, and/or the handle 110 when received within the recess 158C. The distal flange 154C of the rotation assembly 150C is disposed between, and engaged by, a proximal end of the cap cover 120C and a proximal end of the end cap 130C. The distal flange 154C is received within a cavity 133C formed between a proximal end of the cap cover 120C and a proximal end of the end cap 130C. In this instance, the rotation assembly 150C is axially and longitudinally fixed relative to the cap cover 120C and the end cap 130C. It should be understood that, in other examples, the end cap 130C may include additional detents 140C, such as, for example, within the other proximal opening 139C of the body 132C. As noted above, with the cap cover 120C disposed over the end cap 130C, the pair of openings 129C on the body 122C of the cap cover 120C may align with the pair of distal openings 138C on the body 132C of the end cap 130C. In this instance, a fastener (not shown) may be received through the corresponding openings 129C, 138C to fasten the cap cover 120C to the end cap 130C.

According to an exemplary method of using the cap cover 120C, the end cap 130C, and the rotation assembly 150C with the medical system 100 during a procedure, the detent 140C may engage the distal shaft 156C when the rotation assembly 150C is received through a lumen of the end cap 130C. The detent 140C is biased toward the distal shaft 156C and received within at least one of the plurality of recesses 158C. The rotation assembly 150C is configured to move (e.g., push) the detent 140C out from the recess 158C (compressing the spring of the detent 140C) as the distal shaft 156C rotates within the end cap 130C. Rotation of the rotation assembly 150C may cause the detent 140C to exit the recess 158C and be received along an exterior surface (i.e. a space) of the distal shaft 156C disposed between a pair of adjacent recesses 158C.

In this instance, the exterior surface of the distal shaft 156C may abut against the detent 140C, thereby applying an outward radial force onto the detent 140C (compressing the spring). In this instance, the rotation assembly 150C may cause the ball/protrusion of the detent 140C to move out of the recess 158C until the ball/detent is aligned with at least another recess 158C along the distal shaft 156C. Receipt of the detent 140C in the recess 158C on the distal shaft 156C may at least partially fix a radial orientation of the rotation assembly 150C relative to the cap cover 120C, the end cap 130C, and the handle 110. It should be appreciated that the recesses 158C and the detent 140C may collectively inhibit further rotation of the rotation assembly 150C when the detent 140C is biased toward, and received within, at least one recess 158C on the distal shaft 156C.

In the example, the rotation assembly 150C is configured to generate an indexing feedback in response to rotating the rotation assembly 150C relative to the cap cover 120C, the end cap 130C, and/or the handle 110. For example, a user of the medical system 100 may experience a tactile and/or audible feedback at the body 152C of the rotation assembly 150C when the detent 140C of the end cap 130C is received within at least one of the apertures 158C on the distal shaft 156C and/or during rotation of the rotation assembly 150C. In this instance, a user of the medical system 100 may incrementally index a radial position (e.g., orientation) of the medical instrument 170, for example, the cannula 176 and the needle 179 (when disposed within the cannula 176), relative to the handle 110 by receiving the indexing feedback.

It should be appreciated that the plurality of recesses 158C included along the distal shaft 156C form a plurality of predefined angular intervals that the rotation assembly 150C (and the medical instrument 170) may be positioned at. Further, the plurality of recesses 158C on the distal shaft 156C are configured to inhibit movement of the rotation assembly 150C at each of the plurality of predefined angular intervals by engaging the detent 140C within at least one of the plurality of recesses 158C. The detent 140C may provide a force for maintaining the rotation assembly 150C in at least one of the predefined angular intervals. This force may be overcome to allow movement of the rotation assembly 150C and the cannula 176 relative to the handle 110, by applying a predetermined rotative force onto the body 152C greater than the force applied by the spring of the detent 140C.

Figure 7:
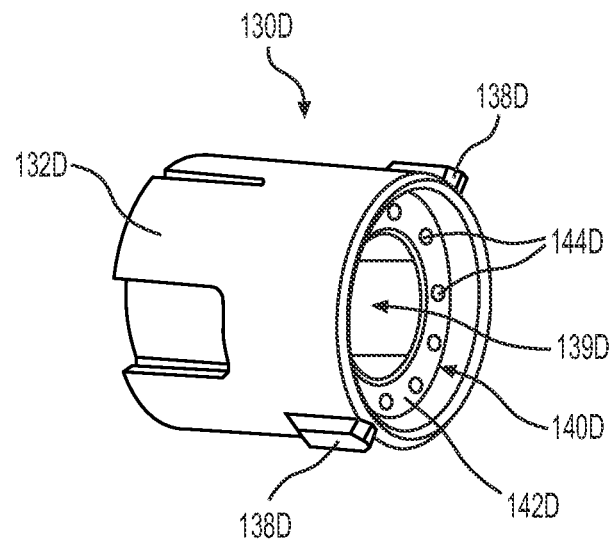
FIG. 7 is a perspective view of another exemplary rotation assembly of the medical device of FIG. 1, according to aspects of this disclosure.
Figure 8:
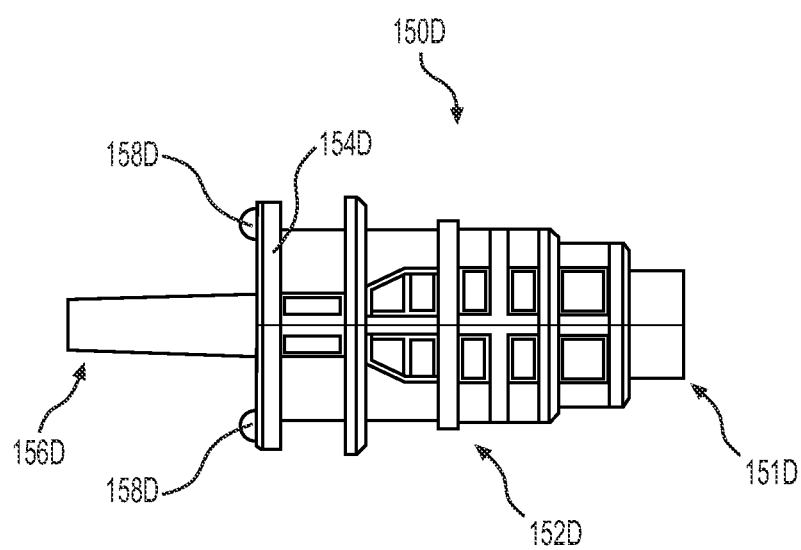
FIG. 8 is a side view of the rotation assembly of FIG. 7, according to aspects of this disclosure.
Figure 9:
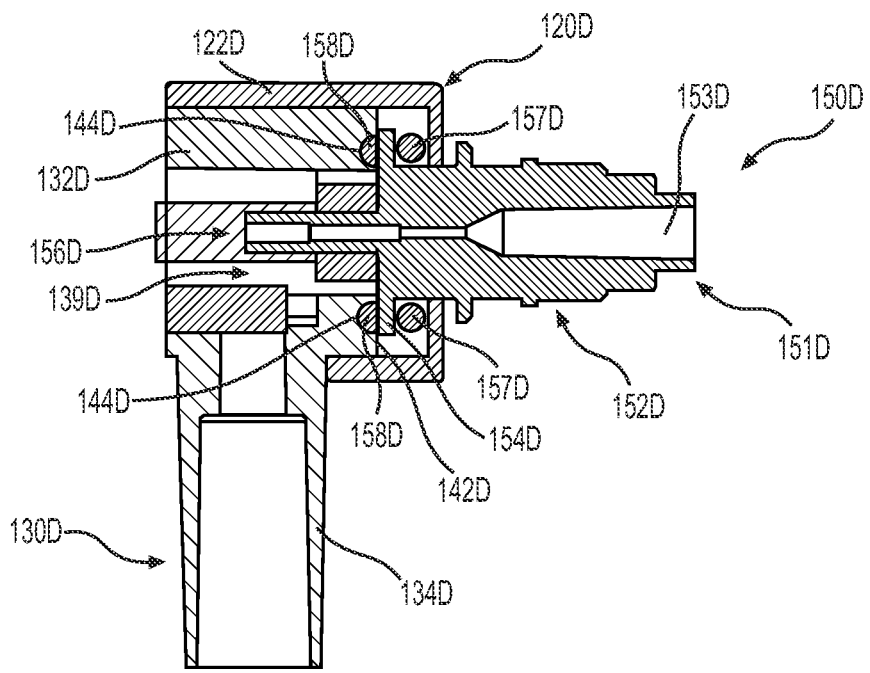
FIG. 9 is a cross-sectional view of the rotation assembly of FIG. 8, according to aspects of this disclosure.

Referring now to FIGS. 7-9, an example of a cap cover 120D, an end cap 130D, and a rotation assembly 150D is shown and described herein. It should be understood that, except as otherwise explicitly noted herein, the cap cover 120D, the end cap 130D, and the rotation assembly 150D may be configured and operable similar to the cap cover 120A, the end cap 130A, and the rotation assembly 150A described above, respectively, such that corresponding numerals are used to identify similar features. For example, referring to FIG. 7, the end cap 130D may include a body 132D defining a lumen 139D extending between a proximal end and a distal end of the body 132D. A proximal end of the body 132D may include an engagement interface 140D having a proximally-facing ledge 142D that extends radially inward into the lumen 139D of the body 132D. The ledge 142D of the engagement interface 140D extends into the lumen 139D to an extent such that the ledge 142D at least partially defines a size (e.g., diameter) and shape of the lumen 139D.

The engagement interface 140D may further include two or more proximally-facing apertures/recesses 144D formed on the ledge 142D. In the example, the engagement interface 140D includes a plurality of apertures/recesses 144D disposed along the ledge 142D and facing a proximal end of the end cap 130D. The plurality of apertures/recesses 144D may be circumferentially spaced apart from one another along the engagement interface 140D, such that adjacent apertures/recesses 144D are offset relative to one another at various suitable intervals. As described further herein, each of the plurality of apertures/recesses 144D are sized and shaped in accordance with a size and shape of one or more components of the rotation assembly 150D, such as, for example, a protrusion 158D. In some examples, one or more of the plurality of apertures/recesses 144D may include different sizes and/or shapes relative to one another corresponding to a size and/or shape of the protrusion 158D (e.g., a sphere, cuboid, and/or other complimentary shapes). It should be appreciated that, in other examples, the ledge 142D on the end cap 130D may include additional and/or fewer apertures/recesses 144D than those shown and described herein without departing from a scope of the disclosure.

Still referring to FIG. 7, the end cap 130D may further include one or more alignment features 138D disposed along an exterior surface of the body 132D. In the example, the end cap 130D includes a pair of alignment features 138D, however, it should be understood that the end cap 130D may include additional and/or fewer alignment features 138D without departing from a scope of the disclosure. The pair of alignment features 138D are configured to engage a corresponding feature of one or more components of the medical device 100 to facilitate an alignment and/or engagement of the end cap 130D to the corresponding component, such as, for example, a rotation assembly cover (not shown), the cap cover 120D, and/or the like. For example, the rotation assembly cover may be a component of the needle 179, and the alignment features 138D may interface with the rotation assembly cover as a rotational stop.

Referring now to FIG. 8, the rotation assembly 150D may include a body 152D defined by a proximal end 151D and a distal flange 154D, with the proximal end 151D including a proximal opening 153D (see FIG. 9) that facilitates access to a lumen of the rotation assembly 150D. Further, the rotation assembly 150D includes a distal shaft 156D extending distally from the distal flange 154D. The rotation assembly 150D differs from the rotation assembly 150A described above in that the distal flange 154D includes one or more distally-facing protrusions 158D formed thereon. The distal flange 154D of the rotation assembly 150D includes a pair of protrusions 158D extending outwardly from an exterior surface of the distal flange 154D opposite of the body 152D. It should be appreciated that, in other examples, the rotation assembly 150D may include additional and/or fewer protrusions 158D along various other suitable surfaces than those shown and described herein. In examples where the rotation assembly 150D includes multiple protrusions 158D, it should be appreciated that the protrusions 158D may be circumferentially spared apart from one another by a distance corresponding to an area between adjacent apertures/recesses 144D along the ledge 142D of the engagement interface 142D.

Referring now to FIG. 9, and as noted above, the protrusion 158D is sized, shaped, and configured to be received within the one or more apertures/recesses 144D along the ledge 142D of the engagement interface 140D when the rotation assembly 150D is received in the end cap 130D. In this instance, the protrusions 158D at least partially maintain the rotation assembly 150D at a fixed radial position (e.g., orientation) relative to the cap cover 120D, the end cap 130D, and/or the handle 110 when received within at least one of the plurality of apertures/recesses 144D on the ledge 142D. The distal flange 154D is received along the ledge 142D of the engagement interface 140D and engages the ledge 142D when the protrusions 158D are received within the apertures/recesses 144D formed thereon.

The distal flange 154D is maintained against the ledge 142D of the end cap 130D by one or more gaskets 157D disposed between an exterior surface of the distal flange 154D, opposite of the ledge 142D, and an inner surface of the cap cover 120D. In the example, the one or more gaskets 157D include an O-ring formed of an elastomer that is configured to force and/or push the distal flange 154D of the rotation assembly 150D against the ledge 142D of the end cap 130D when the cap cover 120D is coupled thereto. In other words, attachment of the cap cover 120D with the end cap 130D may generate a force that thereby restricts movement of the one or more gaskets 157D (e.g., O-ring) and causes an elastic deformation of the one or more gaskets 157D to provide linear movement of the rotation assembly 150D.

Still referring to FIG. 9, the cap cover 120D of the example includes a single gasket 157D, however, it should be appreciated that additional gaskets 157D may be included between the cap cover 120D and the distal flange 154D than those shown and described herein. For example, it should be understood that in other examples the gasket 157D may be omitted from between the cap cover 120D and the rotation assembly 150D entirely, and/or include various other deformable or spring-like devices than the O-ring described herein. Further, and as described in detail below, the gasket 157D is operable to flexibly deform in response to receiving a compressive force applied thereto, such as, for example, the distal flange 154D and/or the cap cover 120D to allow the protrusions 158D to disengage from the apertures/recesses 144D.

According to an exemplary method of using the cap cover 120D, the end cap 130D, and the rotation assembly 150D with the medical system 100 during a procedure, the medical system 100 may initially be inserted into a patient and maneuvered such that the medical instrument 170 received within the handle 110 is positioned adjacent to a target treatment site. With the distal shaft 156D of the rotation assembly 150D extending through a lumen of the end cap 130D, each of the protrusions 158D of the rotation assembly 150D may engage and/or be received in at least one of the plurality of apertures/recesses 144D on the end cap 130D. The protrusions 158D are biased outwardly from the distal flange 154D and received within at least one of the plurality of apertures/recesses 144D on the ledge 142D. The rotation assembly 150D is configured to move (e.g., rotate) the protrusions 158D out from the aperture/recess 144D as the distal shaft 156D rotates within the end cap 130D.

Rotation of the rotation assembly 150D may cause the protrusions 158D to exit the apertures/recesses 144D and be received along an exterior surface of the ledge 142D between a pair of adjacent apertures/recesses 144D. In this instance, the exterior surface of the ledge 142D may abut against the protrusions 158D, thereby applying a proximal force onto the distal flange 154D of the rotation assembly 150D. In this instance, the rotation assembly 150D may move proximally relative to the cap cover 120D and the end cap 130D such that the distal flange 154D abuts against the gasket 157D disposed between the cap cover 120D and the distal flange 154D. As a result, the distal flange 154D may cause the gasket 157D to compress when the pair of protrusions 158D are not received within at least one aperture/recess 144D on the ledge 142D (high energy state), until becoming aligned with at least another aperture/recess 144D (low energy state). Compression of the gasket 157D positions the rotation assembly 150D in a high energy state compared to a low energy state when the pair of protrusions 158D are received within at least one aperture/recess 144D and the gasket 157D is not compressed.

Receipt of at least a portion of the pair of protrusions 158D in the apertures/recesses 144D of the engagement interface 140D may at least partially fix a radial orientation of the rotation assembly 150D relative to the cap cover 120D, the end cap 130D, and the handle 110. It should be appreciated that the apertures/recesses 144D and the protrusions 158D may collectively inhibit further rotation of the rotation assembly 150D when the protrusions 158D are biased toward, and received within, at least one aperture/recess 144D on the ledge 142D. In this instance, the gasket 157D may expand thereby positioning the rotation assembly 150D in the low energy state.

In the example, the rotation assembly 150D is configured to generate an indexing feedback in response to rotating the rotation assembly 150D relative to the cap cover 120D, the end cap 130D, and/or the handle 110. For example, a user of the medical system 100 may experience a tactile and/or audible feedback at the body 152D of the rotation assembly 150D when the protrusions 158D on the distal flange 154D are received within at least one of the apertures/recesses 144D on the ledge 142D of the end cap 130D and/or during rotation of the rotation assembly 150D. In this instance, a user of the medical system 100 may incrementally index a radial position (e.g., orientation) of the medical instrument 170, for example, the cannula 176 and the needle 179 (when disposed within the cannula 176), relative to the handle 110 by receiving the indexing feedback.

It should be appreciated that the plurality of apertures/recesses 144D included along the ledge 142D of the engagement interface 140D form a plurality of predefined angular intervals that the rotation assembly 150D (and the medical instrument 170) may be positioned at. Further, the plurality of apertures/recesses 144D on the end cap 130D are configured to inhibit movement of the rotation assembly 150D at each of the plurality of predefined angular intervals by engaging the protrusions 158D within at least one of the plurality of apertures/recesses 144D. The apertures/recesses 144D and/or the protrusions 158D may collectively provide a force for maintaining the rotation assembly 150D in at least one of the predefined angular intervals. The force may be overcome, to allow movement of the rotation assembly 150D and the cannula 176 relative to the handle 110, by applying a rotational force onto the body 152D greater than a force applied by the apertures/recesses 144D and/or the protrusions 158D, as generated by a compression of the gasket 157D.

Figure 11:
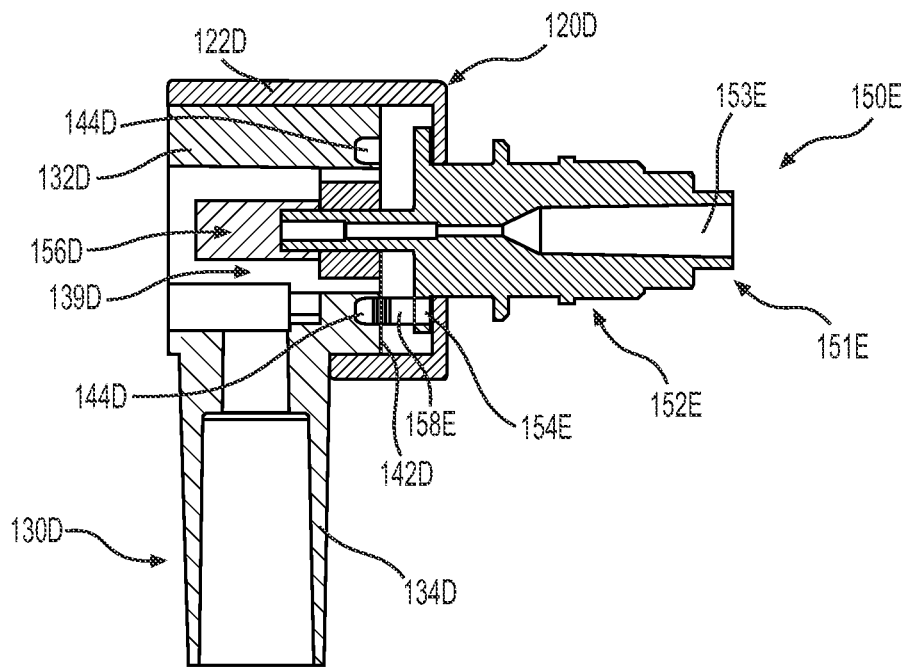
FIG. 11 is a cross-sectional view of the rotation assembly of FIG. 10, according to aspects of this disclosure.

Referring now to FIGS. 10-11, an example of a rotation assembly 150E is shown and described herein. It should be understood that the rotation assembly 150E of the example may be incorporated with the cap cover 120D and the end cap 130D shown and described above. It should further be understood that, except as otherwise explicitly noted herein, the rotation assembly 150E may be configured and operable similar to the rotation assembly 150A described above such that corresponding numerals are used to identify similar features. For example, the rotation assembly 150E may include a body 152E defined by a proximal end 151E and a distal flange 154E, with the proximal end 151E including a proximal opening 153E (see FIG. 10) that facilitates access to a lumen of the rotation assembly 150E. Further, the rotation assembly 150E includes a distal shaft 156E extending distally from the distal flange 154E.

The rotation assembly 150E differs from the rotation assembly 150A described above in that the distal flange 154E includes one or more detents 158E formed thereon or otherwise attached thereto. The distal flange 154E of the rotation assembly 150E includes a detent 158E extending outwardly from an exterior surface of the distal flange 154E opposite of the body 152E. It should be appreciated that, in other examples, the rotation assembly 150E may include additional detents 158E along various other suitable surfaces than those shown and described herein. Further, it should be understood that, in other examples, the one or more detents 158E may be formed on one or more other components of the medical device 100 than the rotation assembly 150E. The detent 158E of the rotation assembly 150E is biased to an extended state relative to the exterior surface of the distal flange 154E, as shown in FIG. 10.

The detent 158E of the rotation assembly 150E is flexibly deformable such that the detent 158E is configured to deform (e.g., compress) from the extended state to a retracted state when, for example, a predetermined force is applied thereto. In some examples, the detent 158E may include a ball and/or protrusion feature coupled to a distal end of a spring and/or biasing mechanism. In this instance, the ball/protrusion at the distal end of the spring may be the portion of the detent 158E received within the apertures/recesses 144D. In other examples, the detent 158E may include an elastic protrusion that is longitudinally expandable and compressible. In other examples, the detent 158E may be a screw that is threaded into the distal flange 154E such that the detent 158E is configured to transition from the extended state to the retracted state by rotating outwardly and/or inwardly relative to the distal flange 154E, respectively.

Referring now to FIG. 11, and as noted above, the detent 158E is sized, shaped, and configured to be received within the one or more apertures/recesses 144D along the ledge 142D of the engagement interface 142D when the rotation assembly 150E is received in the end cap 130D. In this instance, the detent 158E at least partially maintains the rotation assembly 150E at a fixed position (e.g., orientation) relative to the cap cover 120D, the end cap 130D, and/or the handle 110 when received within at least one of the plurality of apertures/recesses 144D on the ledge 142D. The distal flange 154E of the rotation assembly 150E is received along the ledge 142D of the engagement interface 140D and engages the ledge 142D when the detent 158E is received within at least one of the plurality of the apertures/recesses 144D formed thereon.

According to an exemplary method of using the cap cover 120D, the end cap 130D, and the rotation assembly 150E with the medical system 100 during a procedure, the detent 158E may engage and/or be received in at least one of the plurality of apertures/recesses 144D when the distal shaft 156E of the rotation assembly 150E extends through a lumen of the end cap 130D. The detent 158E is biased distally and outwardly from the distal flange 154E and at least partially received within at least one of the plurality of apertures/recesses 144D on the ledge 142D. In this instance, the aperture/recess 144D sized and shaped such that the detent 158E may only partially be disposed within the aperture/recess 144D. Accordingly, the distal flange 154E is offset from the ledge 142D thereby forming a space and/or gap between the distal flange 154E and the ledge 142D when the detent 158E is in the extended state. The rotation assembly 150E is configured to move the detent 158E out from the aperture/recess 144D (compressing the spring of the detent 158E) as the distal shaft 156E rotates within the end cap 130D.

Rotation of the rotation assembly 150E may cause the detent 158E to exit the aperture/recess 144D and be received along an exterior surface of the ledge 142D between a pair of adjacent apertures/recesses 144D. In this instance, the detent 158E may abut against the exterior surface of the ledge 142D, thereby applying a longitudinal proximal force onto the detent 158E of the rotation assembly 150E (compressing the spring). In this instance, the space/gap between the distal flange 154E and the ledge 142D provides a spatial clearance for the detent 158E to transition from the extended state to a retracted state by compressing. It should be appreciated that movement of the rotation assembly 150E relative to the cap cover 120D and the end cap 130D is minimal due to a compression of the detent 158E. Accordingly, the distal flange 154E is offset from the ledge 142D of the engagement interface 140D when the detent 158E is in the retracted state until becoming aligned with at least another aperture/recess 144D. Receipt of at least a portion of the detent 158E in at least one aperture 144D of the engagement interface 140D may at least partially fix a radial orientation of the rotation assembly 150E relative to the cap cover 120D, the end cap 130D, and the handle 110. It should be appreciated that the apertures 144D and the detent 158E may collectively inhibit further rotation of the rotation assembly 150E when the detent 158E is biased toward, and received within, at least one aperture/recess 144D on the ledge 142D.

In the example, the rotation assembly 150E is configured to generate an indexing feedback in response to rotating the rotation assembly 150E relative to the cap cover 120D, the end cap 130D, and/or the handle 110. For example, a user of the medical system 100 may experience a tactile and/or audible feedback at the body 152E of the rotation assembly 150E when the detent 158E on the distal flange 154E is received within at least one of the apertures/recesses 144D on the ledge 142D of the end cap 130D and/or during rotation of the rotation assembly 150E. In this instance, a user of the medical system 100 may incrementally index a radial position (e.g., orientation) of the medical instrument 170, for example, the cannula 176 and the needle 179, relative to the handle 110 by receiving the indexing feedback.

It should be appreciated that the plurality of apertures/recesses 144D included along the ledge 142D of the engagement interface 140D form a plurality of predefined angular intervals that the rotation assembly 150E (and the medical instrument 170) may be positioned at. Further, the plurality of apertures/recesses 144D on the end cap 130D are configured to inhibit movement of the rotation assembly 150E at each of the plurality of predefined angular intervals by engaging the detent 158E within at least one of the plurality of apertures/recesses 144D. The apertures/recesses 144D and/or the detent 158E may provide a collective force for maintaining the rotation assembly 150E in at least one of the predefined angular intervals. The force may be overcome, to allow movement of the rotation assembly 150E and the cannula 176 relative to the handle 110, by applying a rotational force onto the body 152E greater than the force applied by the apertures/recesses 144D and/or the detent 158E.

Figure 12:
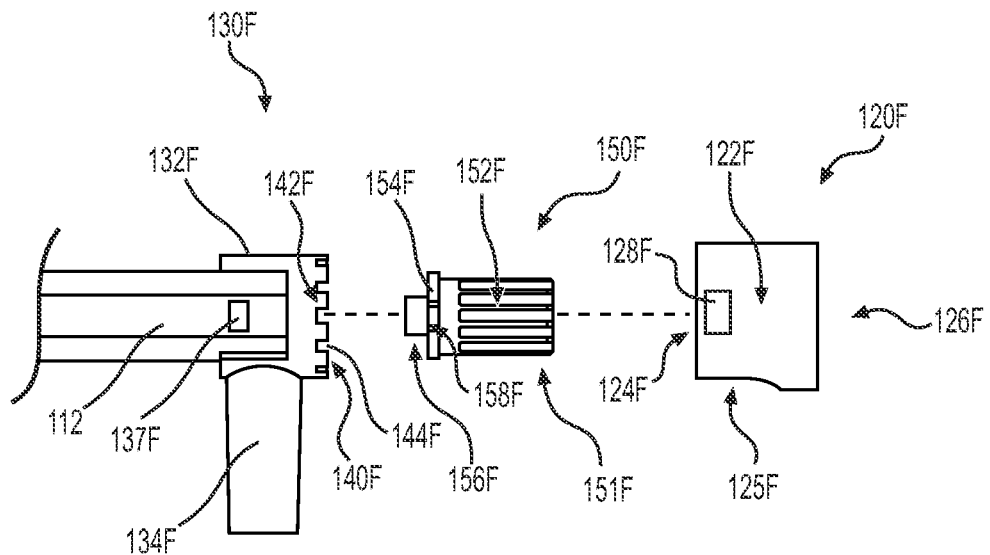
FIG. 12 is an exploded side view of another rotation assembly of the medical device of FIG. 1, according to aspects of this disclosure.

Referring now to FIG. 12, an example of a cap cover 120F, an end cap 130F, and a rotation assembly 150F is shown and described herein. It should be understood that, except as otherwise explicitly noted herein, the cap cover 120F, the end cap 130F, and the rotation assembly 150F may be configured and operable similar to the cap cover 120A, the end cap 130A, and the rotation assembly 150A described above, respectively, such that corresponding numerals are used to identify similar features. For example, the rotation assembly 150F may include a body 152F defined by a proximal end 151F and a distal flange 154F, with the proximal end 151F including a proximal opening 153F (FIGS. 13-14) that facilitates access to a lumen of the rotation assembly 150F. Further, the rotation assembly 150F includes a distal shaft 156F extending distally from the distal flange 154F.

The rotation assembly 150F differs from the rotation assembly 150A described above in that the distal flange 154F includes one or more deflectable and/or flexible arms 158F formed thereon. The distal flange 154F of the rotation assembly 150F includes a pair of flexible arms 158F extending outwardly from a perimeter edge of the distal flange 154F. In the example, each of the pair of flexible arms 158F is sized, shaped, and configured to be received within one or more components of the end cap 130F, such as, for example, an opening 144F. As described in further detail herein, each of the pair of flexible arms 158F is configured to engage one or more components of the end cap 130F when the end cap 130F receives the rotation assembly 150F. For example, the flexible arms 158F are operable to engage a pair of protrusions 142F of the end cap 130F in response to the rotation assembly 150F being inserted into the end cap 130F.

Still referring to FIG. 12, the cap cover 120F may include a body 122F defined by a distal opening 124F and a proximal opening 126F. The distal opening 124F is sized, shaped, and configured to receive the rotation assembly 150F and the cap cover 120F therethrough. The body 122F further includes a side window 125F and one or more apertures 128F along a sidewall of the cap cover 120F. The side window 125F is sized and shaped to receive one or more components of the end cap 130F therethrough, such as, for example, a pin housing 134F. The end cap 130F may include a body 132F having a pin housing 134F extending outwardly therefrom and one or more engagement tabs 137F extending radially outward from the body 132F. The one or more engagement tabs 137F are sized, shaped, and configured to engage a proximal end of the outer body 112 to thereby couple the end cap 130F to the handle 110. Additionally and/or alternatively, the one or more engagement tabs 137F may be configured to engage the one or more apertures 128F formed along the sidewalls of the cap cover 120F to thereby couple the end cap 130F to the cap cover 120F.

The end cap 130F may further include an engagement interface 140F along a proximal end of the end cap 130F. As noted above, the engagement interface 140F of the end cap 130F may include one or more proximally-facing protrusions 142F and one or more proximally-facing recesses 144F formed thereon. It should be appreciated that the protrusions 142F alternate with, form, and define the recesses 144F. The engagement interface 140F includes a plurality of protrusions 142F and a plurality of recesses 144F formed along a proximal end of the body 132F, with at least one recess 144F positioned between an adjacent pair of protrusions 142F. As described in further detail herein, each of the plurality of recesses 144F is sized, shaped, and configured to receive at least one flexible arm 158F of the rotation assembly 150F between an adjacent pair of protrusions 142F when the end cap 130F is coupled to the rotation assembly 150F.

Figure 13:
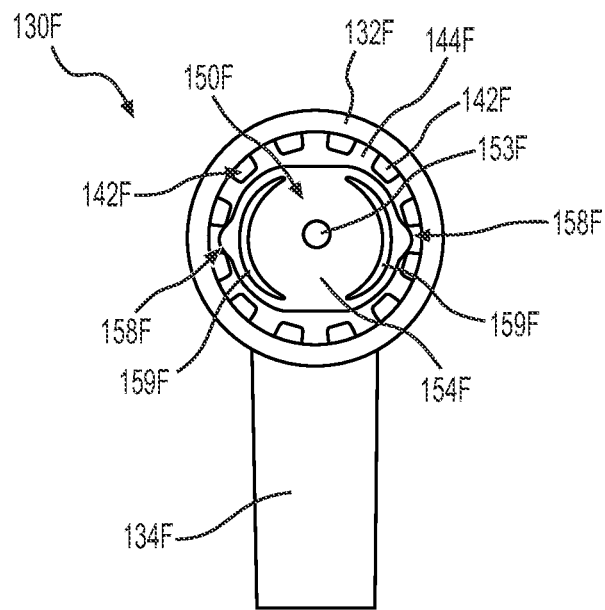
FIG. 13 is a bottom view of the rotation assembly of FIG. 12, according to aspects of this disclosure.

As best seen in FIG. 13, the rotation assembly 150F includes at least one slot 159F disposed between the distal flange 154F and each of the flexible arms 158F. The flexible arms 158F of the rotation assembly 150F are configured to extend outwardly from the distal flange 154F relative to a size, shape, and configuration of the at least one slot 159F. As described further herein, each of the flexible arms 158F is movable relative to the distal flange 154F in response to an expansion and/or compression of the slot 159F disposed therebetween. Accordingly, it should be understood that the flexible arms 158F and/or the slots 159F are deformable relative to the distal flange 154F and that movement of the flexible arms 158F may increase and/or decrease a size of the slots 159F.

Figure 14:
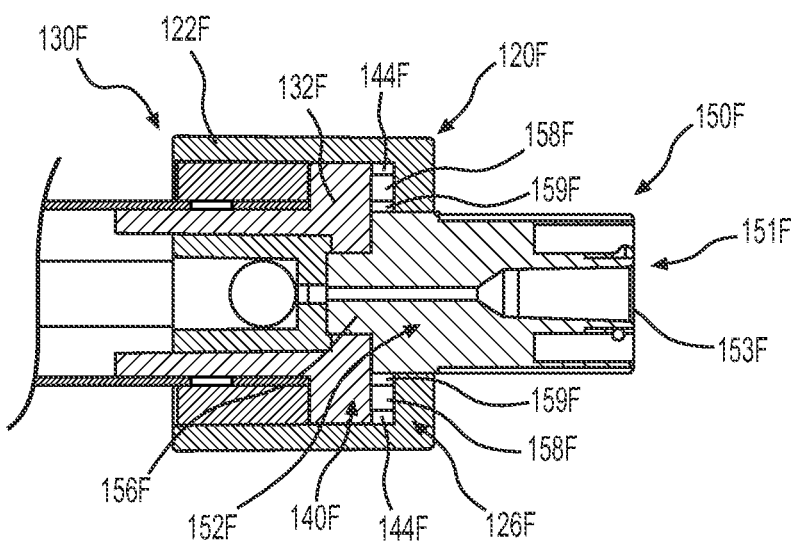
FIG. 14 is a cross-sectional view of the rotation assembly of FIG. 12, according to aspects of this disclosure.

Referring now to FIG. 14, the rotation assembly 150F is depicted within the end cap 130F with the flexible arms 158F received within at least one of the plurality of recesses 144F. In this instance, the flexible arms 158F at least partially maintain the rotation assembly 150F at a fixed radial position (e.g., orientation) relative to the cap cover 120F, the end cap 130F, and/or the handle 110 when received within the recess 144F. The distal flange 154F of the rotation assembly 150F is disposed between, and engaged by, a proximal end of the cap cover 120F and a proximal end of the end cap 130F. In this instance, the rotation assembly 150F is longitudinally and axially fixed relative to the cap cover 120F and the end cap 130F. It should be understood that, in other examples, the rotation assembly 150F may include additional and/or fewer flexible arms 158F on the distal flange 154F.

According to an exemplary method of using the cap cover 120F, the end cap 130F, and the rotation assembly 150F with the medical system 100 during a procedure, the flexible arms 158F of the distal flange 154F may engage the recesses 144F along the engagement interface 140F when the distal shaft 156F of the rotation assembly 150F is received through a lumen of the end cap 130F. The flexible arms 158F are biased outwardly from the distal flange 154F and received within at least one of the plurality of recesses 144F. In this instance, with each of the flexible arms 158F disposed within at least one recess 144F, the flexible arms 158F are maintained in the extended state. The rotation assembly 150F is configured to move the flexible arms 158F out from the recesses 144F as the distal shaft 156F rotates within the end cap 130F.

Rotation of the rotation assembly 150F may cause the flexible arms 158F to move radially inward and exit the recesses 144F and be aligned with at least one protrusion 142F of the engagement interface 140F. In this instance, the flexible arms 158F may abut against the protrusions 142F, thereby applying an inwardly radial force onto the flexible arms 158F. In this instance, the end cap 130F may cause the flexible arms 158F to transition from an extended state to a compressed state until becoming aligned with at least another recess 144F between a pair of protrusions 142F. In the compressed state, the at least one slot 159F disposed between the distal flange 154F and each of the flexible arms 158F deforms in response to the flexible arms 158F moving radially inward toward the distal flange 154F.

Receipt of at least a portion of each of the flexible arms 158F in at least one recess 144F may at least partially fix a radial orientation of the rotation assembly 150F relative to the cap cover 120F, the end cap 130F, and the handle 110. It should be appreciated that the protrusions 142F, the recesses 144F, and the flexible arms 158F may collectively inhibit further rotation of the rotation assembly 150F when the flexible arms 158F are biased toward, and received within, at least one recess 144F on the end cap 130F.

In the example, the rotation assembly 150F is configured to generate an indexing feedback in response to rotating the rotation assembly 150F relative to the cap cover 120F, the end cap 130F, and/or the handle 110. For example, a user of the medical system 100 may experience a tactile and/or audible feedback at the body 152F of the rotation assembly 150F when the flexible arms 158F on the distal flange 154F are received within at least one of the recesses 144F on the end cap 130F and/or during rotation of the rotation assembly 150F. In this instance, a user of the medical system 100 may incrementally index a radial position (e.g., orientation) of the medical instrument 170, for example, the cannula 176 and the needle 179 (when disposed within the cannula 176), relative to the handle 110 by receiving the indexing feedback.

It should be appreciated that the plurality of recesses 144F included along the engagement interface 140F form a plurality of predefined angular intervals that the rotation assembly 150F (and the medical instrument 170) may be positioned at. Further, the plurality of recesses 144F are configured to inhibit movement of the rotation assembly 150F at each of the plurality of predefined angular intervals by engaging the flexible arms 158F between a pair of adjacent protrusions 142F. The protrusions 142F, the recesses 144F, and/or the flexible arms 158F may collectively provide a force for maintaining the rotation assembly 150F in at least one of the predefined angular intervals. The force may be overcome, to allow movement of the rotation assembly 150F and the cannula 176 relative to the handle 110, by applying a rotational force onto the body 152F greater than the force applied by the protrusions 142F, the recesses 144F, and/or the flexible arms 158F.

Each of the aforementioned devices, assemblies, and methods may be used to facilitate access to a target treatment site and provide enhanced control of ancillary tools/devices for use at the target treatment site. By providing a medical device with a rotation assembly capable of controlling a plurality of tools/devices of a medical instrument coupled to the medical device at predefined angular intervals, a user may interact with a target treatment site using the various tools/devices of the medical instrument during a procedure and receive feedback of a position of said tools/devices. In this instance, a user may reduce overall procedure time, increase efficiency of procedures, and/or avoid unnecessary harm to a patient's body caused by limited control of the ancillary tools/devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:
1. A medical device, comprising:
a tool; and
a handle including a rotation assembly, wherein the rotation assembly is configured to rotate the tool relative to the handle at predefined angular intervals and inhibit movement at each of the predefined angular intervals;
wherein:
the rotation assembly includes a plurality of arms and at least one slot, wherein the plurality of arms of the rotation assembly extend radially outward relative to the rotation assembly;
the handle includes a plurality of recesses configured to receive the plurality of arms, wherein the plurality of recesses are proximally-facing;
the plurality of recesses define the predefined angular intervals;
rotational movement of the rotation assembly is inhibited when at least one arm of the plurality of arms is engaged with a recess of the plurality of recesses; and
the at least one slot is configured to expand when the at least one arm of the plurality of arms of the rotation assembly is engaged with the recess of the plurality of recesses of the handle.

2. The medical device of claim 1, wherein the medical device further comprises a sheath extending from the handle, wherein the tool is disposed within the sheath, and wherein the tool is movable relative to the sheath.

3. The medical device of claim 1, wherein the rotation assembly maintains the tool in at least one of the predefined angular intervals to fix the tool relative to the handle; and
wherein the rotation assembly releases the tool from at least one of the predefined angular intervals in response to a predetermined rotational force applied to the rotation assembly.

4. The medical device of claim 1, wherein the rotation assembly is configured to generate a first indexing feedback as the rotation assembly rotates out of a first predefined angular interval, and wherein the first indexing feedback is at least one of a first tactile, audible, or visual feedback.

5. The medical device of claim 4, wherein the rotation assembly is configured to generate a second indexing feedback as the rotation assembly rotates into a second predefined angular interval, wherein the second indexing feedback is at least one of a second tactile, audible, or visual feedback.

6. The medical device of claim 1, wherein the at least one slot is configured to compress when the rotation assembly is rotated from a first predefined angular interval to a second predefined angular interval.

7. A medical device, comprising:
   a tool;
   a handle including a rotation assembly and an end cap, wherein the end cap is configured to receive the rotation assembly, wherein the rotation assembly is configured to rotate the tool in response to rotation of the rotation assembly relative to the end cap,
   wherein:
   the rotation assembly is configured to rotate the tool at predefined angular intervals and inhibit movement at each of the predefined angular intervals;
   the end cap includes a plurality of protrusions defining a plurality of recesses;
   the rotation assembly includes two or more arms extending radially outward from the rotation assembly;
   the end cap inhibits rotational movement of the rotation assembly relative to the end cap when a first arm of the two or more arms is positioned in a first recess of the plurality of recesses and when a second arm of the two or more arms is positioned in a second recess of the plurality of recesses; and
   the rotation assembly includes at least one slot, wherein the at least one slot is configured to deform in response to a radially-inward movement of at least one arm of the two or more arms.

8. The medical device of claim 7, wherein each protrusion of the plurality of protrusions is proximally-facing, and wherein each recess of the plurality of recesses is proximally-facing.

9. The medical device of claim 7, wherein the end cap and the rotation assembly are coupled to a proximal end of the handle.

10. The medical device of claim 7, wherein the handle further includes a cap cover, and wherein the cap cover is configured to couple to the end cap.

11. A medical device, comprising:
   a tool; and
   a handle including a rotation assembly, wherein the rotation assembly is configured to rotate the tool relative to the handle at predefined angular intervals and inhibit movement at each of the predefined angular intervals;
   wherein:
   the handle includes a plurality of arms;
   the plurality of arms of the handle extend radially inward into a lumen of the handle;
   the rotation assembly includes a plurality of recesses configured to receive the plurality of arms;
   the plurality of recesses define the predefined angular intervals; and
   rotational movement of the rotation assembly is inhibited when at least one arm of the plurality of arms is engaged with a recess of the plurality of recesses;
   a distal end of the rotation assembly includes a distal flange;
   the distal flange of the rotation assembly includes one or more flat edges;
   a proximal end of the handle includes one or more ledges; and
   the one or more ledges are configured to interlock with the distal flange to couple the rotation assembly to the handle.

12. The medical device of claim 11, wherein each arm of the plurality of arms of the handle is offset from an adjacent arm of the plurality of arms.

13. The medical device of claim 11, wherein the medical device further comprises a sheath extending from the handle, wherein the tool is disposed within the sheath, and wherein the tool is movable relative to the sheath.

14. The medical device of claim 11, wherein the rotation assembly maintains the tool in at least one of the predefined angular intervals to fix the tool relative to the handle; and
   wherein the rotation assembly releases the tool from at least one of the predefined angular intervals in response to a predetermined rotational force applied to the rotation assembly.

15. The medical device of claim 11, wherein the rotation assembly is configured to generate a first indexing feedback as the rotation assembly rotates out of a first predefined angular interval, and wherein the first indexing feedback is at least one of a first tactile, audible, or visual feedback.

16. The medical device of claim 15, wherein the rotation assembly is configured to generate a second indexing feedback as the rotation assembly rotates into a second predefined angular interval, wherein the second indexing feedback is at least one of a second tactile, audible, or visual feedback.

17. The medical device of claim 11, wherein each recess of the plurality of recesses is proximally-facing.

18. The medical device of claim 11, wherein the handle further includes an end cap, wherein the end cap is configured to receive the rotation assembly, wherein the rotation assembly is configured to rotate the tool in response to rotation of the rotation assembly relative to the end cap.

* * * * *